(12) United States Patent
Suo

(10) Patent No.: US 8,609,339 B2
(45) Date of Patent: Dec. 17, 2013

(54) SYSTEM AND METHOD FOR EMULSION BREAKING AND RECOVERY OF BIOLOGICAL ELEMENTS

(75) Inventor: Yue Suo, New Haven, CT (US)

(73) Assignee: 454 Life Sciences Corporation, Branford, CT (US)

( * ) Notice: Subject to any disclaimer, the term of this patent is extended or adjusted under 35 U.S.C. 154(b) by 282 days.

(21) Appl. No.: 12/879,493

(22) Filed: Sep. 10, 2010

(65) Prior Publication Data

US 2011/0087016 A1 Apr. 14, 2011

Related U.S. Application Data

(60) Provisional application No. 61/250,332, filed on Oct. 9, 2009.

(51) Int. Cl.
*C12Q 1/68* (2006.01)
*C07H 19/167* (2006.01)
*C07H 19/173* (2006.01)

(52) U.S. Cl.
USPC ............. 435/6.12; 536/27.62; 536/27.63

(58) Field of Classification Search
None
See application file for complete search history.

(56) References Cited

U.S. PATENT DOCUMENTS

| | | | |
|---|---|---|---|
| 6,210,891 B1 | 4/2001 | Nyren et al. ................ 435/6 |
| 6,258,568 B1 | 7/2001 | Nyren ...................... 435/91.1 |
| 6,274,320 B1 | 8/2001 | Rothberg et al. ............ 435/6 |
| 6,828,100 B1 | 12/2004 | Ronaghi .................... 435/6 |
| 7,211,390 B2 | 5/2007 | Rothberg et al. ............ 435/6 |
| 7,323,305 B2 | 1/2008 | Leamon et al. ............. 435/6 |
| 7,575,865 B2 | 8/2009 | Leamon et al. ............. 435/6 |
| 7,601,499 B2 | 10/2009 | Berka et al. ............... 435/6 |
| 7,622,280 B2 | 11/2009 | Holliger et al. ........... 435/91.2 |
| 7,638,276 B2 | 12/2009 | Griffiths et al. ............ 435/6 |
| 7,682,816 B2 | 3/2010 | Kim et al. ................ 435/283.1 |
| 7,842,457 B2 * | 11/2010 | Berka et al. .............. 435/6.16 |
| 7,927,797 B2 * | 4/2011 | Nobile et al. ............. 435/6.16 |
| 2004/0185484 A1 | 9/2004 | Costa et al. ............... 506/14 |
| 2005/0079510 A1 | 4/2005 | Berka et al. ............... 506/16 |
| 2005/0227264 A1 | 10/2005 | Nobile et al. ............. 435/6 |
| 2006/0228721 A1 | 10/2006 | Leamon et al. ............ 435/6 |
| 2009/0053724 A1 | 2/2009 | Roth et al. ................ 435/6 |
| 2009/0105959 A1 | 4/2009 | Braverman et al. ......... 702/19 |
| 2009/0203086 A1 | 8/2009 | Chen et al. .............. 435/91.5 |
| 2009/0233291 A1 | 9/2009 | Chen et al. ............... 435/6 |
| 2010/0003687 A1 | 1/2010 | Simen et al. ............. 435/6 |
| 2011/0003701 A1 | 1/2011 | Ferreri et al. ............ 506/9 |

FOREIGN PATENT DOCUMENTS

WO WO 2007/149432 12/2007
WO WO 2008/115427 9/2008

OTHER PUBLICATIONS

Merrifield (1964), Biochemistry, 3:1385-1390.
Zhigang et al. (2001), Journal of Chemical Technology and Biotechnology, 76:757-763.
International Search Report for PCT/EP2010/006140 mailed Mar. 22, 2011.

* cited by examiner

*Primary Examiner* — Lawrence E Crane
(74) *Attorney, Agent, or Firm* — Mintz Levin Cohn Ferris Glovsky and Popeo, P.C.; Ivor R. Elrifi; Christina K. Stock, Esq.

(57) ABSTRACT

An embodiment of a method for extracting biological material from an emulsion is described that comprises the steps of a) breaking an emulsion comprising a plurality of aqueous droplets in a continuous phase of an oil using a solvent to produce a combined aqueous-oil mixture, where the solvent disrupts the aqueous droplets which release a plurality of biological elements each immobilized on a substrate into the combined aqueous-oil mixture; b) introducing an inorganic salt to the combined aqueous-oil mixture causing a phase separation of the mixture into a first phase comprising an aqueous solution and the biological elements and a second phase comprising the solvent and the oil; c) extracting the first phase from the second phase; and d) collecting the substrate immobilized biological elements from the first phase.

10 Claims, 2 Drawing Sheets

SYSTEM AND METHOD FOR EMULSION BREAKING AND RECOVERY OF BIOLOGICAL ELEMENTS

CROSS-REFERENCE TO RELATED APPLICATIONS

This application is related to and claims priority from U.S. Provisional Patent Application Ser. No. 61/250,332, titled "System and Method for Emulsion Breaking and Recovery of Biological Elements" filed Oct. 9, 2009, which is hereby incorporated by reference herein in its entirety for all purposes.

FIELD OF THE INVENTION

The invention provides systems, methods, reagents, and kits for breaking aqueous emulsion microdroplets dispersed in an oil phase and isolation of nucleic acid products contained therein. More specifically, the invention relates to the isolation of amplified nucleic acid products from a thermostable emulsion

BACKGROUND OF THE INVENTION

The development of methods and kits for performing biological processes within the droplets of "water-in-oil" emulsions have made a tremendous contribution to the development of high throughput analysis technologies, particularly for the high throughput nucleic acid sequencing technologies that employ nucleic acid material amplified within emulsion droplets. It will be appreciated that such emulsions have been successfully employed for a number of uses that include in-vitro transcription/translation, what is referred to as directed evolution, and amplification processes. For example, each aqueous droplet of an emulsion is a micro compartment or microreactor within which the process of interest may be conducted in isolation where the many thousands of the droplets are executing the process in a massively parallel fashion. In the more specific example of nucleic acid amplification, the process can proceed with very high efficiency and without contamination from neighboring droplets. In most applications the type of amplification process performed in aqueous emulsion droplets is the well known Polymerase Chain Reaction (PCR) method which benefits from the highly efficient heat transfer characteristics of the emulsion as well as the biological compatibility of typical water-in-oil emulsions. In addition, many emulsion embodiments for generating sequencable material are amenable to the inclusion of solid phase substrates such as microspheres (i.e. bead type substrates) upon which the amplification products can be immobilized. This effectively sequesters the amplification products so that when the emulsions droplets are broken to recover the products each species of product can be kept separated from the others and subsequently used as a clonal population.

In general water-in-oil emulsions for use in biological contexts are disrupted or "broken" and the biological material released from the droplets is then purified for subsequent use preferably without destruction or modification of the biological integrity or composition. Traditionally, the water-in-oil emulsions have been broken using a solvent such as isopropanol and the components separated by centrifugation methods. In embodiments that employ the centrifugation method with amplified nucleic acid populations sequestered to beads it is preferable to repeat the centrifugation process several times to remove the oil and surfactants that is followed by rinsing with a buffer solution and further centrifugation the remove the isopropanol. The traditional centrifuge based process is time consuming and not amenable to transitioning to commercially available lab automation platforms.

Therefore, it is the object of the described invention to provide a more efficient and automatable process for extracting biological elements from an emulsion without causing damage or changing the characteristics of those elements.

SUMMARY OF THE INVENTION

Embodiments of the invention relate to the determination of the sequence of nucleic acids. More particularly, embodiments of the invention relate to methods and systems for correcting errors in data obtained during the sequencing of nucleic acids by SBS.

An embodiment of a method for extracting biological material from an emulsion is described that comprises the steps of a) breaking an emulsion comprising a plurality of aqueous droplets in a continuous phase of an oil using a solvent to produce a combined aqueous-oil mixture, where the solvent disrupts the aqueous droplets which release a plurality of biological elements each immobilized on a substrate into the combined aqueous-oil mixture; b) introducing an inorganic salt to the combined aqueous-oil mixture causing a phase separation of the mixture into a first phase comprising an aqueous solution and the biological elements and a second phase comprising the solvent and the oil; c) extracting the first phase from the second phase; and d) collecting the substrate immobilized biological elements from the first phase.

The above embodiments and implementations are not necessarily inclusive or exclusive of each other and may be combined in any manner that is non-conflicting and otherwise possible, whether they be presented in association with a same, or a different, embodiment or implementation. The description of one embodiment or implementation is not intended to be limiting with respect to other embodiments and/or implementations. Also, any one or more function, step, operation, or technique described elsewhere in this specification may, in alternative implementations, be combined with any one or more function, step, operation, or technique described in the summary. Thus, the above embodiment and implementations are illustrative rather than limiting.

BRIEF DESCRIPTION OF THE DRAWINGS

The above and further features will be more clearly appreciated from the following detailed description when taken in conjunction with the accompanying drawings. In the drawings, like reference numerals indicate like structures, elements, or method steps and the leftmost digit of a reference numeral indicates the number of the figure in which the references element first appears (for example, element 101 appears first in FIG. 1). All of these conventions, however, are intended to be typical or illustrative, rather than limiting.

DETAILED DESCRIPTION OF THE INVENTION

Figure 1:
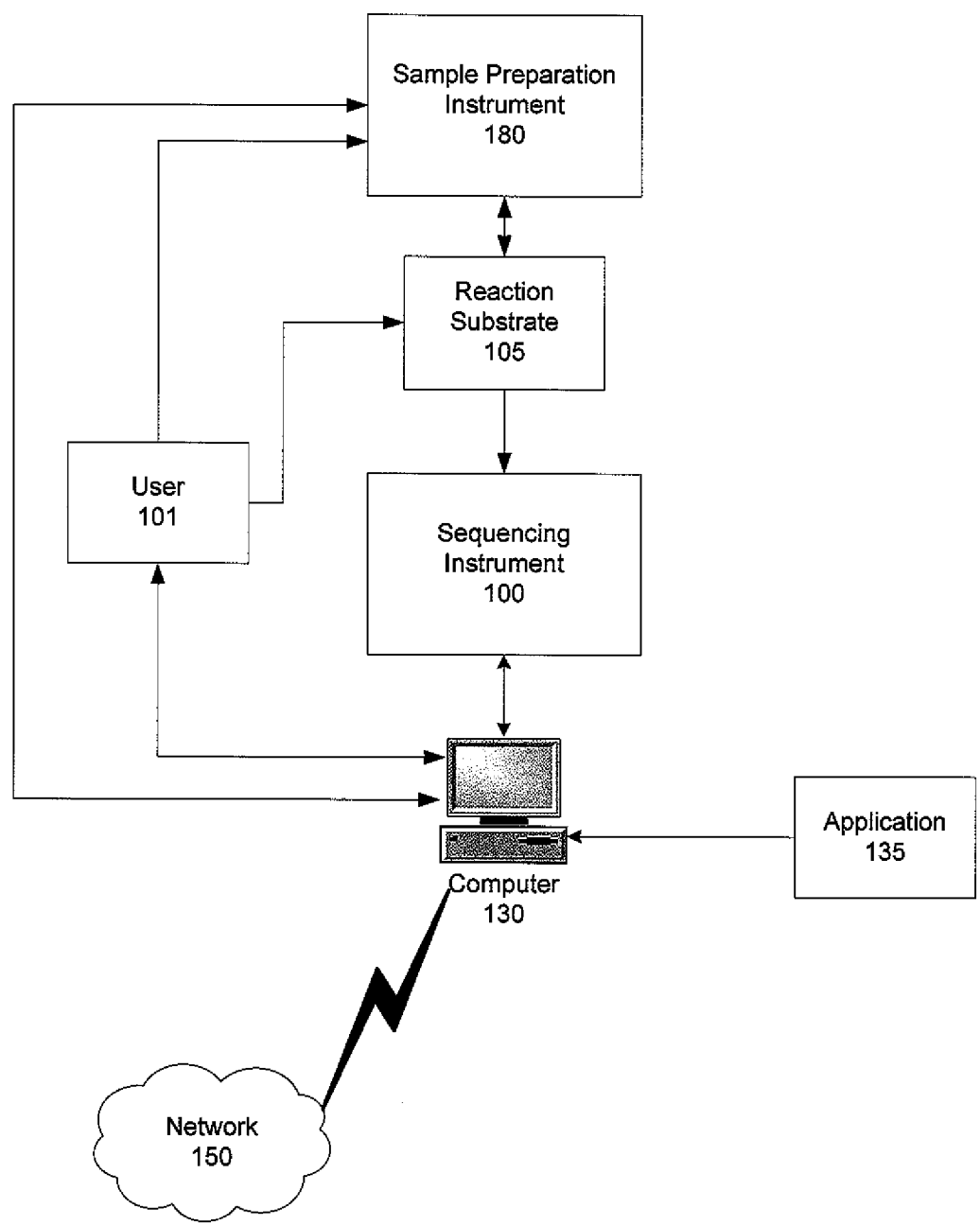
FIG. 1 is a functional block diagram of one embodiment of a sequencing instrument under computer control and a reaction substrate.

As will be described in greater detail below, embodiments of the presently described invention include systems, methods, and kits for breaking emulsions and recovery of biological elements contained therein. In particular, embodiments of the invention relate to water-in-oil emulsions used for amplification of nucleic acid template molecules and the recovery of the amplified populations for use in high throughput technology such as nucleic acid sequencing.

a. General

The term "flowgram" generally refers to a graphical representation of sequence data generated by SBS methods, particularly pyrophosphate based sequencing methods (also referred to as "pyrosequencing") and may be referred to more specifically as a "pyrogram".

The term "read" or "sequence read" as used herein generally refers to the entire sequence data obtained from a single nucleic acid template molecule or a population of a plurality of substantially identical copies of the template nucleic acid molecule.

The terms "run" or "sequencing run" as used herein generally refer to a series of sequencing reactions performed in a sequencing operation of one or more template nucleic acid molecules.

The term "flow" as used herein generally refers to a serial or iterative cycle of addition of solution to an environment comprising a template nucleic acid molecule, where the solution may include a nucleotide species for addition to a nascent molecule or other reagent, such as buffers or enzymes that may be employed in a sequencing reaction or to reduce carryover or noise effects from previous flow cycles of nucleotide species.

The term "flow cycle" as used herein generally refers to a sequential series of flows where a nucleotide species is flowed once during the cycle (i.e. a flow cycle may include a sequential addition in the order of T, A, C, G nucleotide species, although other sequence combinations are also considered part of the definition). Typically, the flow cycle is a repeating cycle having the same sequence of flows from cycle to cycle.

The term "read length" as used herein generally refers to an upper limit of the length of a template molecule that may be reliably sequenced. There are numerous factors that contribute to the read length of a system and/or process including, but not limited to the degree of GC content in a template nucleic acid molecule.

The term "test fragment" or "TF" as used herein generally refers to a nucleic acid element of known sequence composition that may be employed for quality control, calibration, or other related purposes.

The term "primer" as used herein generally refers to an oligonucleotide that acts as a point of initiation of DNA synthesis under conditions in which synthesis of a primer extension product complementary to a nucleic acid strand is induced in an appropriate buffer at a suitable temperature. A primer is preferably a single stranded oligodeoxyribonucleotide.

A "nascent molecule" generally refers to a DNA strand which is being extended by the template-dependent DNA polymerase by incorporation of nucleotide species which are complementary to the corresponding nucleotide species in the template molecule.

The terms "template nucleic acid", "template molecule", "target nucleic acid", or "target molecule" generally refer to a nucleic acid molecule that is the subject of a sequencing reaction from which sequence data or information is generated.

The term "nucleotide species" as used herein generally refers to the identity of a nucleic acid monomer including purines (Adenine, Guanine) and pyrimidines (Cytosine, Uracil, Thymine) typically incorporated into a nascent nucleic acid molecule.

The term "monomer repeat" or "homopolymers" as used herein generally refers to two or more sequence positions comprising the same nucleotide species (i.e. a repeated nucleotide species).

The term "homogeneous extension" as used herein, generally refers to the relationship or phase of an extension reaction where each member of a population of substantially identical template molecules is homogenously performing the same extension step in the reaction.

The term "completion efficiency" as used herein generally refers to the percentage of nascent molecules that are properly extended during a given flow.

The term "incomplete extension rate" as used herein generally refers to the ratio of the number of nascent molecules that fail to be properly extended over the number of all nascent molecules.

The term "genomic library" or "shotgun library" as used herein generally refers to a collection of molecules derived from and/or representing an entire genome (i.e. all regions of a genome) of an organism or individual.

The term "amplicon" as used herein generally refers to selected amplification products, such as those produced from Polymerase Chain Reaction or Ligase Chain Reaction techniques.

The term "variant" or "allele" as used herein generally refers to one of a plurality of species each encoding a similar sequence composition, but with a degree of distinction from each other. The distinction may include any type of genetic variation known to those of ordinary skill in the related art, that include, but are not limited to, polymorphisms such as single nucleotide polymorphisms (SNPs), insertions or deletions (the combination of insertion/deletion events are also referred to as "indels"), differences in the number of repeated sequences (also referred to as tandem repeats), and structural variations.

The term "allele frequency" or "allelic frequency" as used herein generally refers to the proportion of all variants in a population that is comprised of a particular variant.

The term "key sequence" or "key element" as used herein generally refers to a nucleic acid sequence element (typically of about 4 sequence positions, i.e., TGAC or other combination of nucleotide species) associated with a template nucleic acid molecule in a known location (i.e., typically included in a ligated adaptor element) comprising known sequence composition that is employed as a quality control reference for sequence data generated from template molecules. The sequence data passes the quality control if it includes the known sequence composition associated with a Key element in the correct location.

The term "keypass" or "keypass well" as used herein generally refers to the sequencing of a full length nucleic acid test sequence of known sequence composition (i.e., a "test fragment" or "TF" as referred to above) in a reaction well, where the accuracy of the sequence derived from TF sequence and/or Key sequence associated with the TF or in an adaptor associated with a target nucleic acid is compared to the known sequence composition of the TF and/or Key and used to measure of the accuracy of the sequencing and for quality control. In typical embodiments, a proportion of the total number of wells in a sequencing run will be keypass wells which may, in some embodiments, be regionally distributed.

The term "blunt end" as used herein is interpreted consistently with the understanding of one of ordinary skill in the related art, and generally refers to a linear double stranded nucleic acid molecule having a end that terminates with a pair of complementary nucleotide base species, where a pair of blunt ends is typically compatible for ligation to each other.

The term "sticky end" or "overhang" as used herein is interpreted consistently with the understanding of one of ordinary skill in the related art, and generally refers to a linear double stranded nucleic acid molecule having one or more unpaired nucleotide species at the end of one strand of the molecule, where the unpaired nucleotide species may exist on either strand and include a single base position or a plurality of base positions (also sometimes referred to as "cohesive end").

The term "bead" or "bead substrate" as used herein generally refers to any type of bead of any convenient size and fabricated from any number of known materials such as cellulose, cellulose derivatives, acrylic resins, glass, silica gels, polystyrene, gelatin, polyvinyl pyrrolidone, co-polymers of vinyl and acrylamide, polystyrene cross-linked with divinyl-benzene or the like (as described, e.g., in Merrifield, Biochemistry 1964, 3, 1385-1390), polyacrylamides, latex gels, polystyrene, dextran, rubber, silicon, plastics, nitrocellulose, natural sponges, silica gels, control pore glass, metals, cross-linked dextrans (e.g., Sephadex™) agarose gel (Sepharose™), and other solid phase bead supports known to those of skill in the art.

Some exemplary embodiments of systems and methods associated with sample preparation and processing, generation of sequence data, and analysis of sequence data are generally described below, some or all of which are amenable for use with embodiments of the presently described invention. In particular, the exemplary embodiments of systems and methods for preparation of template nucleic acid molecules, amplification of template molecules, generating target specific amplicons and/or genomic libraries, sequencing methods and instrumentation, and computer systems are described.

In typical embodiments, the nucleic acid molecules derived from an experimental or diagnostic sample must be prepared and processed from its raw form into template molecules amenable for high throughput sequencing. The processing methods may vary from application to application, resulting in template molecules comprising various characteristics. For example, in some embodiments of high throughput sequencing, it is preferable to generate template molecules with a sequence or read length that is at least the length a particular sequencing method can accurately produce sequence data for. In the present example, the length may include a range of about 25-30 base pairs, about 50-100 base pairs, about 200-300 base pairs, about 350-500 base pairs, greater than 500 base pairs, or other length amenable for a particular sequencing application. In some embodiments, nucleic acids from a sample, such as a genomic sample, are fragmented using a number of methods known to those of ordinary skill in the art. In preferred embodiments, methods that randomly fragment (i.e. do not select for specific sequences or regions) nucleic acids and may include what is referred to as nebulization or sonication methods. It will, however, be appreciated that other methods of fragmentation, such as digestion using restriction endonucleases, may be employed for fragmentation purposes. Also in the present example, some processing methods may employ size selection methods known in the art to selectively isolate nucleic acid fragments of the desired length.

Also, it is preferable in some embodiments to associate additional functional elements with each template nucleic acid molecule. The elements may be employed for a variety of functions including, but not limited to, primer sequences for amplification and/or sequencing methods, quality control elements (i.e. such as Key elements or other type of quality control element), unique identifiers (also referred to as a multiplex identifier or "MID") that encode various associations such as with a sample of origin or patient, or other functional element.

For example, some embodiments of the described invention comprise associating one or more embodiments of an MID element having a known and identifiable sequence composition with a sample, and coupling the embodiments of MID element with template nucleic acid molecules from the associated samples. The MID coupled template nucleic acid molecules from a number of different samples are pooled into a single "Multiplexed" sample or composition that can then be efficiently processed to produce sequence data for each MID coupled template nucleic acid molecule. The sequence data for each template nucleic acid is de-convoluted to identify the sequence composition of coupled MID elements and association with sample of origin identified. In the present example, a multiplexed composition may include representatives from about 384 samples, about 96 samples, about 50 samples, about 20 samples, about 16 samples, about 10 samples, or other number of samples. Each sample may be associated with a different experimental condition, treatment, species, or individual in a research context. Similarly, each sample may be associated with a different tissue, cell, individual, condition, drug or other treatment in a diagnostic context. Those of ordinary skill in the related art will appreciate that the numbers of samples listed above are for the purposes of example and thus should not be considered limiting.

In preferred embodiments, the sequence composition of each MID element is easily identifiable and resistant to introduced error from sequencing processes. Some embodiments of MID element comprise a unique sequence composition of nucleic acid species that has minimal sequence similarity to a naturally occurring sequence. Alternatively, embodiments of a MID element may include some degree of sequence similarity to naturally occurring sequence.

Also, in preferred embodiments the position of each MID element is known relative to some feature of the template nucleic acid molecule and/or adaptor elements coupled to the template molecule. Having a known position of each MID is useful for finding the MID element in sequence data and interpretation of the MID sequence composition for possible errors and subsequent association with the sample of origin. For example, some features useful as anchors for positional relationship to MID elements may include, but are not limited to, the length of the template molecule (i.e. the MID element is known to be so many sequence positions from the 5' or 3' end), recognizable sequence markers such as a Key element and/or one or more primer elements positioned adjacent to a MID element. In the present example, The Key and primer elements generally comprise a known sequence composition that typically does not vary from sample to sample in the multiplex composition and may be employed as positional references for searching for the MID element. An analysis algorithm implemented by application 135 may be executed on computer 130 to analyze generated sequence data for each MID coupled template to identify the more easily recognizable Key and/or primer elements, and extrapolate from those positions to identify a sequence region presumed to include the sequence of the MID element. Application 135 may then process the sequence composition of the presumed region and possibly some distance away in the flanking regions to positively identify the MID element and its sequence composition.

Some or all of the described functional elements may be combined into adaptor elements that are coupled to nucleotide sequences in certain processing steps. For example, some embodiments may associate priming sequence elements or regions comprising complementary sequence composition to primer sequences employed for amplification and/or sequencing. Further, the same elements may be employed for what may be referred to as "strand selection" and immobilization of nucleic acid molecules to a solid phase substrate. In some embodiments, two sets of priming sequence regions (hereafter referred to as priming sequence A, and priming sequence B) may be employed for strand selection, where only single strands having one copy of priming sequence A and one copy of priming sequence B is selected and included as the prepared sample. In alternative embodiments, design characteristics of the adaptor elements eliminate the need for strand selection. The same priming sequence regions may be employed in methods for amplification and immobilization where, for instance, priming sequence B may be immobilized upon a solid substrate and amplified products are extended therefrom.

Additional examples of sample processing for fragmentation, strand selection, and addition of functional elements and adaptors are described in U.S. patent application Ser. No. 10/767,894, titled "Method for preparing single-stranded DNA libraries", filed Jan. 28, 2004; U.S. patent application Ser. No. 12/156,242, titled "System and Method for Identification of Individual Samples from a Multiplex Mixture", filed May 29, 2008; and U.S. patent application Ser. No. 12/380,139, titled "System and Method for Improved Processing of Nucleic Acids for Production of Sequencable Libraries", filed Feb. 23, 2009, each of which is hereby incorporated by reference herein in its entirety for all purposes.

Various examples of systems and methods for performing amplification of template nucleic acid molecules to generate populations of substantially identical copies are described. It will be apparent to those of ordinary skill that it is desirable in some embodiments of SBS to generate many copies of each nucleic acid element to generate a stronger signal when one or more nucleotide species is incorporated into each nascent molecule associated with a copy of the template molecule. There are many techniques known in the art for generating copies of nucleic acid molecules such as, for instance, amplification using what are referred to as bacterial vectors, "Rolling Circle" amplification (described in U.S. Pat. Nos. 6,274,320 and 7,211,390, incorporated by reference above) and Polymerase Chain Reaction (PCR) methods, each of the techniques are applicable for use with the presently described invention. One PCR technique that is particularly amenable to high throughput applications include what are referred to as emulsion PCR methods (also referred to as emPCR™ methods).

Typical embodiments of emulsion PCR methods include creating a stable emulsion of two immiscible substances creating aqueous droplets within which reactions may occur. In particular, the aqueous droplets of an emulsion amenable for use in PCR methods may include a first fluid, such as a water based fluid suspended or dispersed as droplets (also referred to as a discontinuous phase) within another fluid, such as a hydrophobic fluid (also referred to as a continuous phase) that typically includes some type of oil. Examples of oil that may be employed include, but are not limited to, mineral oils, silicone based oils, or fluorinated oils.

Further, some emulsion embodiments may employ surfactants that act to stabilize the emulsion, which may be particularly useful for specific processing methods such as PCR. Some embodiments of surfactant may include one or more of a silicone or fluorinated surfactant. For example, one or more non-ionic surfactants may be employed that include, but are not limited to, sorbitan monooleate (also referred to as Span™ 80), polyoxyethylenesorbitsan monooleate (also referred to as Tween™ 80), or in some preferred embodiments, dimethicone copolyol (also referred to as Abil® EM90), polysiloxane, polyalkyl polyether copolymer, polyglycerol esters, poloxamers, and PVP/hexadecane copolymers (also referred to as Unimer U-151), or in more preferred embodiments, a high molecular weight silicone polyether in cyclopentasiloxane (also referred to as DC 5225C available from Dow Corning).

The droplets of an emulsion may also be referred to as compartments, microcapsules, microreactors, microenvironments, or other name commonly used in the related art. The aqueous droplets may range in size depending on the composition of the emulsion components or composition, contents contained therein, and formation technique employed. The described emulsions create the microenvironments within which chemical reactions, such as PCR, may be performed. For example, template nucleic acids and all reagents necessary to perform a desired PCR reaction may be encapsulated and chemically isolated in the droplets of an emulsion. Additional surfactants or other stabilizing agent may be employed in some embodiments to promote additional stability of the droplets as described above. Thermocycling operations typical of PCR methods may be executed using the droplets to amplify an encapsulated nucleic acid template resulting in the generation of a population comprising many substantially identical copies of the template nucleic acid. In some embodiments, the population within the droplet may be referred to as a "clonally isolated", "compartmentalized", "sequestered", "encapsulated", or "localized" population. Also in the present example, some or all of the described droplets may further encapsulate a solid substrate such as a bead for attachment of template and amplified copies of the template, amplified copies complementary to the template, or combination thereof. Further, the solid substrate may be enabled for attachment of other type of nucleic acids, reagents, labels, or other molecules of interest.

Embodiments of an emulsion useful with the presently described invention may include a very high density of droplets or microcapsules enabling the described chemical reactions to be performed in a massively parallel way. Additional examples of emulsions employed for amplification and their uses for sequencing applications are described in U.S. Pat. Nos. 7,638,276; 7,622,280; and U.S. patent application Ser. Nos. 10/767,899; and 11/045,678, each of which is hereby incorporated by reference herein in its entirety for all purposes.

Also embodiments sometimes referred to as Ultra-Deep Sequencing, generate target specific amplicons for sequencing may be employed with the presently described invention that include using sets of specific nucleic acid primers to amplify a selected target region or regions from a sample comprising the target nucleic acid. Further, the sample may include a population of nucleic acid molecules that are known or suspected to contain sequence variants comprising sequence composition associated with a research or diagnostic utility where the primers may be employed to amplify and provide insight into the distribution of sequence variants in the sample. For example, a method for identifying a sequence variant by specific amplification and sequencing of multiple alleles in a nucleic acid sample may be performed. The nucleic acid is first subjected to amplification by a pair of PCR primers designed to amplify a region surrounding the region of interest or segment common to the nucleic acid population. Each of the products of the PCR reaction (first amplicons) is subsequently further amplified individually in separate reaction vessels such as an emulsion based vessel described above. The resulting amplicons (referred to herein as second amplicons), each derived from one member of the first population of amplicons, are sequenced and the collection of sequences are used to determine an allelic frequency of one or more variants present. Importantly, the method does not require previous knowledge of the variants present and can typically identify variants present at <1% frequency in the population of nucleic acid molecules.

Some advantages of the described target specific amplification and sequencing methods include a higher level of sensitivity than previously achieved. Further, embodiments that employ high throughput sequencing instrumentation, such as for instance embodiments that employ what is referred to as a PicoTiterPlate® array (also sometimes referred to as a PTP™ plate or array) of wells provided by 454 Life Sciences Corporation, the described methods can be employed to generate sequence composition for over 100,000, over 300,000, over 500,000, or over 1,000,000 nucleic acid regions per run or experiment and may depend, at least in part, on user preferences such as lane configurations enabled by the use of gaskets, etc. Also, the described methods provide a sensitivity of detection of low abundance alleles which may represent 1% or less of the allelic variants. Another advantage of the methods includes generating data comprising the sequence of the analyzed region. Importantly, it is not necessary to have prior knowledge of the sequence of the locus being analyzed.

Additional examples of target specific amplicons for sequencing are described in U.S. patent application Ser. No. 11/104,781, titled "Methods for determining sequence variants using ultra-deep sequencing", filed Apr. 12, 2005; PCT Patent Application Serial No. US 2008/003424, titled "System and Method for Detection of HIV Drug Resistant Variants", filed Mar. 14, 2008; and U.S. patent application Ser. No. 12/456,528, titled "System and Method for Detection of HIV Tropism Variants", filed Jun. 17, 2009, each of which is hereby incorporated by reference herein in its entirety for all purposes.

Further, embodiments of sequencing may include Sanger type techniques, techniques generally referred to as Sequencing by Hybridization (SBH), Sequencing by Ligation (SBL), or Sequencing by Incorporation (SBI) techniques. Further, the sequencing techniques may include what is referred to as polony sequencing techniques; nanopore, waveguide and other single molecule detection techniques; or reversible terminator techniques. As described above, a preferred technique may include Sequencing by Synthesis methods. For example, some SBS embodiments sequence populations of substantially identical copies of a nucleic acid template and typically employ one or more oligonucleotide primers designed to anneal to a predetermined, complementary position of the sample template molecule or one or more adaptors attached to the template molecule. The primer/template complex is presented with a nucleotide species in the presence of a nucleic acid polymerase enzyme. If the nucleotide species is complementary to the nucleic acid species corresponding to a sequence position on the sample template molecule that is directly adjacent to the 3' end of the oligonucleotide primer, then the polymerase will extend the primer with the nucleotide species. Alternatively, in some embodiments the primer/template complex is presented with a plurality of nucleotide species of interest (typically A, G, C, and T) at once, and the nucleotide species that is complementary at the corresponding sequence position on the sample template molecule directly adjacent to the 3' end of the oligonucleotide primer is incorporated. In either of the described embodiments, the nucleotide species may be chemically blocked (such as at the 3'-O position) to prevent further extension, and need to be deblocked prior to the next round of synthesis. It will also be appreciated that the process of adding a nucleotide species to the end of a nascent molecule is substantially the same as that described above for addition to the end of a primer.

As described above, incorporation of the nucleotide species can be detected by a variety of methods known in the art, e.g. by detecting the release of pyrophosphate (PPi) using an enzymatic reaction process to produce light or via detection of PH change (examples described in U.S. Pat. Nos. 6,210,891; 6,258,568; and 6,828,100, each of which is hereby incorporated by reference herein in its entirety for all purposes), or via detectable labels bound to the nucleotides. Some examples of detectable labels include but are not limited to mass tags and fluorescent or chemiluminescent labels. In typical embodiments, unincorporated nucleotides are removed, for example by washing. Further, in some embodiments the unincorporated nucleotides may be subjected to enzymatic degradation such as, for instance, degradation using the apyrase or pyrophosphatase enzymes as described in U.S. patent application Ser. No. 12/215,455, titled "System and Method for Adaptive Reagent Control in Nucleic Acid Sequencing", filed Jun. 27, 2008; and Ser. No. 12/322,284, titled "System and Method for Improved Signal Detection in Nucleic Acid Sequencing", filed Jan. 29, 2009; each of which is hereby incorporated by reference herein in its entirety for all purposes.

In the embodiments where detectable labels are used, they will typically have to be inactivated (e.g. by chemical cleavage or photobleaching) prior to the following cycle of synthesis. The next sequence position in the template/polymerase complex can then be queried with another nucleotide species, or a plurality of nucleotide species of interest, as described above. Repeated cycles of nucleotide addition, extension, signal acquisition, and washing result in a determination of the nucleotide sequence of the template strand. Continuing with the present example, a large number or population of substantially identical template molecules (e.g. $10^3$, $10^4$, $10^5$, $10^6$ or $10^7$ molecules) are typically analyzed simultaneously in any one sequencing reaction, in order to achieve a signal which is strong enough for reliable detection.

In addition, it may be advantageous in some embodiments to improve the read length capabilities and qualities of a sequencing process by employing what may be referred to as a "paired-end" sequencing strategy. For example, some embodiments of sequencing method have limitations on the total length of molecule from which a high quality and reliable read may be generated. In other words, the total number of sequence positions for a reliable read length may not exceed 25, 50, 100, or 500 bases depending on the sequencing embodiment employed. A paired-end sequencing strategy extends reliable read length by separately sequencing each end of a molecule (sometimes referred to as a "tag" end) that comprise a fragment of an original template nucleic acid molecule at each end joined in the center by a linker sequence. The original positional relationship of the template fragments is known and thus the data from the sequence reads may be recombined into a single read having a longer high quality read length. Further examples of paired-end sequencing embodiments are described in U.S. Pat. No. 7,601,499, titled "Paired end sequencing"; and in U.S. patent application Ser. No. 12/322,119, titled "Paired end sequencing", filed Jan. 28, 2009, each of which is hereby incorporated by reference herein in its entirety for all purposes.

Some examples of SBS apparatus may implement some or all of the methods described above and may include one or more of a detection device such as a charge coupled device (i.e., CCD camera) or confocal type architecture, a microfluidics chamber or flow cell, a reaction substrate, and/or a pump and flow valves. Taking the example of pyrophosphate based sequencing, embodiments of an apparatus may employ a chemiluminescent detection strategy that produces an inherently low level of background noise.

In some embodiments, the reaction substrate for sequencing may include a planar substrate such as a slide type substrate, an Ion-Sensitive Field Effect Transistor (also referred to as "ISFET"), or waveguide type reaction substrate that in some embodiments may comprise well type structures. Further the reaction substrate may include what is referred to as a PTP™ array available from 454 Life Sciences Corporation, as described above, formed from a fiber optics faceplate that is acid-etched to yield hundreds of thousands or more of very small wells each enabled to hold a population of substantially identical template molecules (i.e., some preferred embodiments comprise about 3.3 million wells on a 70×75 mm PTP™ array at a 35 μm well to well pitch). In some embodiments, each population of substantially identical template molecule may be disposed upon a solid substrate, such as a bead, each of which may be disposed in one of said wells. For example, an apparatus may include a reagent delivery element for providing fluid reagents to the PTP plate holders, as well as a CCD type detection device enabled to collect photons of light emitted from each well on the PTP plate. An example of reaction substrates comprising characteristics for improved signal recognition is described in U.S. Pat. No. 7,682,816, titled "THIN-FILM COATED MICROWELL ARRAYS AND METHODS OF MAKING SAME", filed Aug. 30, 2005, which is hereby incorporated by reference herein in its entirety for all purposes. Further examples of apparatus and methods for performing SBS type sequencing and pyrophosphate sequencing are described in U.S. Pat. No. 7,323,305 and U.S. patent application Ser. No. 11/195,254, both of which are incorporated by reference above.

In addition, systems and methods may be employed that automate one or more sample preparation processes, such as the emPCR™ process described above. For example, automated systems may be employed to provide an efficient solution for generating an emulsion for emPCR processing, performing PCR Thermocycling operations, and enriching for successfully prepared populations of nucleic acid molecules for sequencing. Examples of automated sample preparation systems are described in U.S. patent application Ser. No. 11/045,678, titled "Nucleic acid amplification with continuous flow emulsion", filed Jan. 28, 2005, which is hereby incorporated by reference herein in its entirety for all purposes.

Also, the systems and methods of the presently described embodiments of the invention may include implementation of some design, analysis, or other operation using a computer readable medium stored for execution on a computer system. For example, several embodiments are described in detail below to process detected signals and/or analyze data generated using SBS systems and methods where the processing and analysis embodiments are implementable on computer systems.

An exemplary embodiment of a computer system for use with the presently described invention may include any type of computer platform such as a workstation, a personal computer, a server, or any other present or future computer. It will, however, be appreciated by one of ordinary skill in the art that the aforementioned computer platforms as described herein are specifically configured to perform the specialized operations of the described invention and are not considered general purpose computers. Computers typically include known components, such as a processor, an operating system, system memory, memory storage devices, input-output controllers, input-output devices, and display devices. It will also be understood by those of ordinary skill in the relevant art that there are many possible configurations and components of a computer and may also include cache memory, a data backup unit, and many other devices.

Display devices may include display devices that provide visual information, this information typically may be logically and/or physically organized as an array of pixels. An interface controller may also be included that may comprise any of a variety of known or future software programs for providing input and output interfaces. For example, interfaces may include what are generally referred to as "Graphical User Interfaces" (often referred to as GUI's) that provides one or more graphical representations to a user. Interfaces are typically enabled to accept user inputs using means of selection or input known to those of ordinary skill in the related art.

In the same or alternative embodiments, applications on a computer may employ an interface that includes what are referred to as "command line interfaces" (often referred to as CLI's). CLI's typically provide a text based interaction between an application and a user. Typically, command line interfaces present output and receive input as lines of text through display devices. For example, some implementations may include what are referred to as a "shell" such as Unix Shells known to those of ordinary skill in the related art, or Microsoft Windows Powershell that employs object-oriented type programming architectures such as the Microsoft.NET framework.

Those of ordinary skill in the related art will appreciate that interfaces may include one or more GUI's, CLI's or a combination thereof.

A processor may include a commercially available processor such as a Celeron®, Core™, or Pentium® processor made by Intel Corporation, a SPARC® processor made by Sun Microsystems, an Athlon™, Sempron™, Phenom™, or Opteron™ processor made by AMD corporation, or it may be one of other processors that are or will become available. Some embodiments of a processor may include what is referred to as Multi-core processor and/or be enabled to employ parallel processing technology in a single or multi-core configuration. For example, a multi-core architecture typically comprises two or more processor "execution cores". In the present example, each execution core may perform as an independent processor that enables parallel execution of multiple threads. In addition, those of ordinary skill in the related will appreciate that a processor may be configured in what is generally referred to as 32 or 64 bit architectures, or other architectural configurations now known or that may be developed in the future.

A processor typically executes an operating system, which may be, for example, a Windows®-type operating system (such as Windows® XP, Windows Vista®, or Windows®_7) from the Microsoft Corporation; the Mac OS X operating system from Apple Computer Corp. (such as Mac OS X v10.6 "Snow Leopard" operating systems); a Unix® or Linux-type operating system available from many vendors or what is referred to as an open source; another or a future operating system; or some combination thereof. An operating system interfaces with firmware and hardware in a well-known manner, and facilitates the processor in coordinating and executing the functions of various computer programs that may be written in a variety of programming languages. An operating system, typically in cooperation with a processor, coordinates and executes functions of the other components of a computer. An operating system also provides scheduling, input-output control, file and data management, memory management, and communication control and related services, all in accordance with known techniques.

System memory may include any of a variety of known or future memory storage devices. Examples include any commonly available random access memory (RAM), magnetic medium, such as a resident hard disk or tape, an optical medium such as a read and write compact disc, or other memory storage device. Memory storage devices may include any of a variety of known or future devices, including a compact disk drive, a tape drive, a removable hard disk drive, USB or flash drive, or a diskette drive. Such types of memory storage devices typically read from, and/or write to, a program storage medium (not shown) such as, respectively, a compact disk, magnetic tape, removable hard disk, USB or flash drive, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory and/or the program storage device used in conjunction with memory storage device.

In some embodiments, a computer program product is described comprising a computer usable medium having control logic (computer software program, including program code) stored therein. The control logic, when executed by a processor, causes the processor to perform functions described herein. In other embodiments, some functions are implemented primarily in hardware using, for example, a hardware state machine. Implementation of the hardware state machine so as to perform the functions described herein will be apparent to those skilled in the relevant arts.

Input-output controllers could include any of a variety of known devices for accepting and processing information from a user, whether a human or a machine, whether local or remote. Such devices include, for example, modem cards, wireless cards, network interface cards, sound cards, or other types of controllers for any of a variety of known input devices. Output controllers could include controllers for any of a variety of known display devices for presenting information to a user, whether a human or a machine, whether local or remote. In the presently described embodiment, the functional elements of a computer communicate with each other via a system bus. Some embodiments of a computer may communicate with some functional elements using network or other types of remote communications.

As will be evident to those skilled in the relevant art, an instrument control and/or a data processing application, if implemented in software, may be loaded into and executed from system memory and/or a memory storage device. All or portions of the instrument control and/or data processing applications may also reside in a read-only memory or similar device of the memory storage device, such devices not requiring that the instrument control and/or data processing applications first be loaded through input-output controllers. It will be understood by those skilled in the relevant art that the instrument control and/or data processing applications, or portions of it, may be loaded by a processor in a known manner into system memory, or cache memory, or both, as advantageous for execution.

Also, a computer may include one or more library files, experiment data files, and an internet client stored in system memory. For example, experiment data could include data related to one or more experiments or assays such as detected signal values, or other values associated with one or more SBS experiments or processes. Additionally, an internet client may include an application enabled to accesses a remote service on another computer using a network and may for instance comprise what are generally referred to as "Web Browsers". In the present example, some commonly employed web browsers include Microsoft® Internet Explorer 8 available from Microsoft Corporation, Mozilla Firefox® 3.6 from the Mozilla Corporation, Safari 4 from Apple Computer Corp., Google Chrome from the Google™ Corporation, or other type of web browser currently known in the art or to be developed in the future. Also, in the same or other embodiments an internet client may include, or could be an element of, specialized software applications enabled to access remote information via a network such as a data processing application for biological applications.

A network may include one or more of the many various types of networks well known to those of ordinary skill in the art. For example, a network may include a local or wide area network that employs what is commonly referred to as a TCP/IP protocol suite to communicate. A network may include a network comprising a worldwide system of interconnected computer networks that is commonly referred to as the internet, or could also include various intranet architectures. Those of ordinary skill in the related arts will also appreciate that some users in networked environments may prefer to employ what are generally referred to as "firewalls" (also sometimes referred to as Packet Filters, or Border Protection Devices) to control information traffic to and from hardware and/or software systems. For example, firewalls may comprise hardware or software elements or some combination thereof and are typically designed to enforce security policies put in place by users, such as for instance network administrators, etc.

b. Embodiments of the Presently Described Invention

As described above embodiments of the described invention are directed to improved systems, methods, and kits for processing emulsions to safely and efficiently extract the biological products contained therein. The described embodiments can be applied to recover the aqueous phase (or non-aqueous phase) from an emulsion system broken using isopropanol or other organic solvent through what is referred to as a "salting out" effect. It will be appreciated that the described embodiments offer substantial processing improvements over traditional methods because they are highly efficient, maintain biological integrity, and are amenable for execution by automated/robotic type platforms.

In a typical sequencing embodiment one or more instrument elements may be employed to execute one or more process steps. For example, embodiments of a sequencing method may be implemented using instrumentation to automate and carry out some or all process steps. FIG. 1 provides an illustrative example of sequencing instrument 100 that for sequencing processes requiring capture of optical signals typically comprise an optic subsystem and a fluidic subsystem for execution of sequencing reactions and data capture that occur on reaction substrate 105. It will, however, be appreciated that for sequencing processes requiring other modes of data capture (i.e. pH, temperature, electrochemical, etc.) a subsystem for the mode of data capture may be employed which are known to those of ordinary skill in the related art. Embodiments of sequencing instrument 100 employed to execute sequencing processes may further include various additional components not illustrated in FIG. 1 such as microprocessor and/or microcontroller components for local control of some functions.

In some embodiments samples may be optionally prepared for sequencing in an automated or partially automated fashion using sample preparation instrument 180 configured to perform some or all of the necessary preparation for sequencing using instrument 100. Examples of sample preparation instruments may include robotic platforms such as those available from Hamilton Robotics, Beckman Coulter, or Caliper Life Sciences. Further, as illustrated in FIG. 1 sequencing instrument 100 may be operatively linked to one or more external computer components such as computer 130 that may for instance execute system software or firmware such as application 135 that may provide instructional control of one or more of the instruments such as sequencing instrument 100 or sample preparation instrument 180, and/or data analysis functions. Computer 130 may be additionally operatively connected to other computers or servers via network 150 that may enable remote operation of instrument systems and the export of large amounts of data to systems capable of storage and processing. In the present example, sequencing instrument 100 and/or computer 130 may include some or all of the components and characteristics of the embodiments generally described above.

Traditional methods for breaking emulsions that contain biological material have generally employed the use of isopropanol or other non-toxic solvent to compromise the integrity of aqueous droplets emulsified in biologically compatible oil thus releasing the contents of each droplet into solution, a process typically referred to as emulsion "breaking". It will be appreciated that if the biological material is not sequestered (i.e. by attachment to a substrate or other means of sequestration) in some way the result is a mixing of all biological material throughout the volume. Thus, in preferred embodiments the biological material is sequestered to a substrate within the droplets prior to release, where the substrates, such as bead substrates, can then be separated from the components of the emulsion that are not necessary for, or detrimental to, further use (i.e. oil, surfactants, etc.). In the described traditional embodiments high-speed centrifugation has been generally applied to extract beads out of the emulsion. Typically, this step needs to be repeated several times to separate the oil and surfactant materials away from the beads followed by buffer rinses and further centrifugation steps to remove the solvent. Thus, it will be appreciated that the traditional methods are very time consuming and the requirement of centrifugation steps limit the ability to employ low-cost lab automation platforms.

Embodiments of the described invention provide an easy, fast and cost-effective means to separate the aqueous phase from the oil phase after breaking with isopropanol, or similarly effective solvent, for extraction of the solvent from the aqueous phase by what is referred to by those of ordinary skill as the salting out effect. The result is a complete phase separation which enables efficient isolation of the nucleic acid bound substrates. For example, some embodiments of the invention employ hydrophilic beads that preferentially remain in the aqueous phase after the phase separation step which can be recovered with a filter tube and vacuum pump apparatus. In the present example lab automation using commercially available platforms becomes feasible.

Those of ordinary skill in the related art appreciate that the process of salting out isopropanol from aqueous solutions is generally accepted as a way to separate and concentrate isopropanol. An example is described by Zhigang et al.; *Separation of isopropanol from aqueous solution by salting-out extraction* (2001), J. Chemical Technology & Biotechnology, vol. 76 pp 757-763, which is hereby incorporated by reference herein in its entirety for all purposes. However, the salting out process employed in the described invention is different from the prior art methods in that it is employed to force separation of the solvent, surfactant, and oil from the aqueous phase for the purpose of recovering biological material. For example, once the biological processing steps have been completed in the emulsion, isopropanol or other compatible solvent is added to break the droplets and release the biological material. In the present example, an inorganic salt is added to the broken emulsion mixture producing separation of the oil and aqueous phases. In some embodiments, granular inorganic salt may be employed however in alternative embodiments it may be preferable to add the salt in a solution phase (i.e. dissolved in water) which improves the diffusion of the salt within the broken emulsion mixture and increases the rate of phase separation. It is also generally desirable to mechanically mix the solution such as by vortexing or shaking after salt addition to thoroughly distribute the salt throughout the solution. In the described embodiments a variety of biologically compatible solvents may be employed such as isopropanol, ethanol, etc. Further, any type of inorganic salt is effective, depending at least in part upon the type of solvent used, that include but are not limited to NaCl, KCl, LiCl, $Na_2SO_4$, Potassium Carbonate, Ammonium Sulfate, etc.

Continuing the example from above when the inorganic salt is added to the broken emulsion mixture, the water molecules are attracted by the salt ions and are thus less available to interact with the solvent, resulting in the clearly defined separation of the solvent and oil/surfactants (i.e. oil phase) from the aqueous/salt (i.e. aqueous phase). In the preferred embodiments, the hydrophilic beads stay in the aqueous phase due to the surface properties of the beads. It is important to note that the density of the aqueous phase is lower than the density of the oil phase thus resulting in the aqueous phase as a top layer and the oil phase as a bottom layer. Further, the density of the beads in many embodiments is typically higher than the aqueous phase and lower than the oil phase and thus after phase separation the beads are generally positioned at or near the phase interface between the top and bottom layers where subsequent recovery of the beads is relatively easy. In some embodiments a vacuum pump and filter tubes can be used to remove the aqueous phase and trap the beads in a filter element that allows the fluid to pass through, which can be implemented on automated processing platforms such as commercially available robotic platforms that include the Biomek® FX Laboratory Automation Workstation available from Beckman Coulter, Inc., the Sciclone ALH 3000 Liquid Handling Workstation available from Caliper Life Sciences, or other compatible lab automation platform. Also, because there is complete recovery of the aqueous phase there is a small chance for loss of beads and valuable biological resources.

In some embodiments an additional step may be added which improves the extraction of the aqueous phase. For example, after separation of the aqueous and oil phases, a 3rd phase layer can be introduced between the first aqueous and second oil phases to produce an additional phase "gap". Importantly, the material introduced to produce the "gap" phase should be incompatible to mixing with either the aqueous or oil phases to create a clearly defined separation between those phases. In the present example, after the salting process has separated the aqueous and oil phases a volume of high viscosity silicone oil may be slowly introduced between the aqueous and non-aqueous phases using methods known in the art such as pipetting. This further separates the beads in the aqueous phase from the oil phase and provides for easier extraction of the beads where some of the gap phase may be acceptably recovered with the beads most of which easily passes through a filter element. The volume of material introduced to form the gap phase may be dependent upon the size or degree of the desired gap with respect to the volume of the container. In some embodiments, the composition of oil introduced as the gap phase may be the same as the oil used to produce the emulsion which is known to be biologically compatible and typically amenable for use with available filtration apparatus, however there still exists a density difference between the oil phase and the gap phase due to the additional components in the emulsion oil phase (i.e. solvent and surfactant) and thus mixing between the third gap and second oil phases is inhibited. Similarly, mixing between the first aqueous and the third gap phases is inhibited due to density differences and typically the bead substrates remain in the aqueous phase. It may also be desirable in some embodiments to additionally rinse the recovered nucleic acid bound substrates to remove any undesirable residual components. For instance, if a gap phase is used it may be desirable to rinse the recovered substrates with a buffer solution to remove any residual oil. In some embodiments it may also be desirable to combine the buffer with a surfactant (such as the surfactant types used in the emulsion) to aid in removal of residual oil and/or other residual components.

Figure 2:
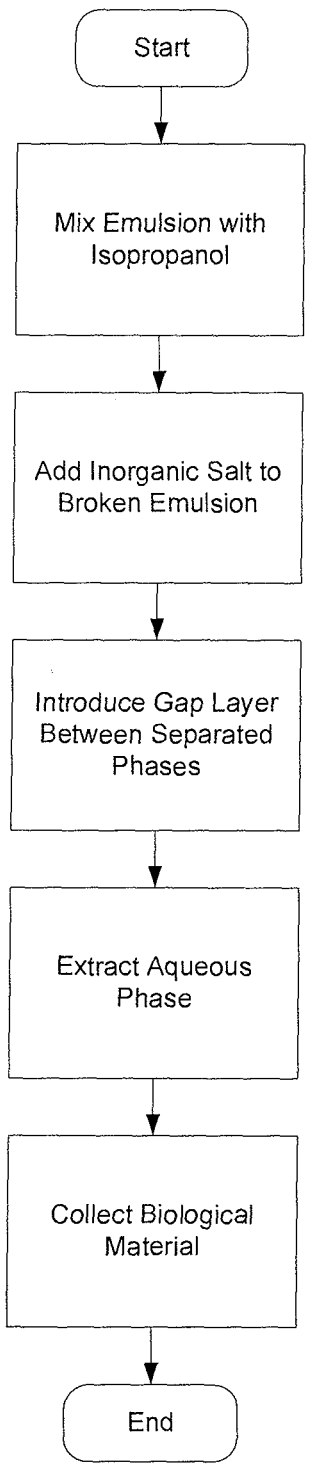
FIG. 2 is a functional block diagram of one embodiment of a method for extracting biological elements from an emulsion using a salt out process.

For example, FIG. 2 provides an illustrative example of a method for extracting nucleic acid beads from an emulsion using a salt out process. As illustrated, a post-PCR emulsion with individual droplets containing hydrophilic beads having an immobilized population of nucleic acid molecules amplified from a single template molecule is thoroughly mixed with isopropanol at about a 1:1 volume ratio. After the majority of aqueous droplets of the emulsion have been broken, a volume of inorganic salt solution such as 5M NaCl, is added and the complete volume, as illustrated, mixed and allowed to rest for the phase separation process to occur (~5 minutes). The concentration and/or volume of inorganic salt solution necessary may vary depending upon the volume of the broken emulsion components where the final concentration of the inorganic salt in the combined mixture is the important factor which is indicated by complete phase separation (i.e. aqueous phase does not have "milky" appearance). Also illustrated is the optional step of slow introduction of 20 cst (cst or centistoke is a measure of kinematic viscosity) silicone oil into the separated aqueous and oil phases to create a gap phase of a desired distance between the aqueous and oil phases. Next as illustrated, the extraction of the entire aqueous phase and in some cases a portion of the gap phase is performed. The biological material can then be collected by the addition of deionized (also referred to as DI) water to dilute the extracted aqueous solution and trapping the bead substrates with a 5 μm filter using a vacuum pump.

EXAMPLES

Example 1

Emulsion Breaking and Solvent Removal Through Salt-Out Effects

Enrichment: (Control: The Traditional Centrifugation Protocol; New: The Salt-Out Protocol)

Beads recovered with the salt-out protocol enriched equally well or better than bead recovery with the traditional protocol.

| Sample | Breaking method | Enrichment ratio* |
|---|---|---|
| 1 | control_A | 9.0% |
| 2 | new_A | 14.4% |
| 3 | new_A | 17.8% |
| 4 | control_B | 7.3% |
| 5 | new_B | 11.2% |
| 6 | new_B | 8.1% |

*The Enrichment ratio refers to the total number of beads added to the emPCR process to the number of beads recovered with amplified nucleic acid products Sequencing Amplified Nucleic Acid Populations from Recovered Beads:

Beads recovered with the salt-out protocol and the traditional protocol show comparable sequencing results

| Sample | Lane | Raw Wells | Keypass (% Raw Wells) | Passed Filter (% Keypass) | Avg Length | Total Bases | 100% | ≥98% | ≥95% |
|---|---|---|---|---|---|---|---|---|---|
| 1 | 1 | 151678 | 150009 0.989 | 91316 0.6206 | 381.17 | 34,806,726 bp | 0.0959 | 0.6931 | 0.8355 |
| 2 | 2 | 127064 | 125662 0.989 | 82776 0.6751 | 365.64 | 30,265,992 bp | 0.2239 | 0.8873 | 0.9436 |
| 3 | 3 | 121400 | 120036 0.9888 | 80423 0.6863 | 385.31 | 30,987,714 bp | 0.1022 | 0.767 | 0.8922 |
| 4 | 4 | 149606 | 148190 0.9905 | 88393 0.6074 | 406.21 | 35,906,207 bp | 0.1131 | 0.7537 | 0.8667 |
| 5 | 5 | 117312 | 115841 0.9875 | 73485 0.6517 | 400.81 | 29,453,481 bp | 0.0853 | 0.7682 | 0.8924 |
| 6 | 6 | 126016 | 124734 0.9898 | 80074 0.6554 | 390.95 | 31,304,613 bp | 0.0694 | 0.7572 | 0.9062 |

Samples 1 and 4 are control and Samples 2, 3, 5, and 6 are new using fragments of known sequence composition where the new Samples demonstrate comparable sequencing accuracy to control Samples as demonstrated at least for ≥95% and ≥98% accuracy of the sequence composition determined from the Samples compared to the known composition.

Having described various embodiments and implementations, it should be apparent to those skilled in the relevant art that the foregoing is illustrative only and not limiting, having been presented by way of example only. Many other schemes for distributing functions among the various functional elements of the illustrated embodiment are possible. The functions of any element may be carried out in various ways in alternative embodiments.

What is claimed is:

1. A method for extraction of solid-phase immobilized nucleic acids from an emulsion, comprising the steps of:
   a) breaking an emulsion comprising a plurality of aqueous droplets in a continuous phase of an oil by application of an organic solvent to produce a combined aqueous-oil mixture, wherein the organic solvent disrupts the aqueous droplets releasing a plurality of nucleic acids each immobilized on a bead substrate into the broken emulsion mixture;
b) introducing an inorganic salt to the broken emulsion mixture causing a phase separation of the mixture into a first phase comprising an aqueous solution and the bead substrate immobilized nucleic acids and a second phase comprising the solvent and the oil;
c) extracting the first phase from the second phase; and
d) collecting the bead substrate immobilized nucleic acids from the first phase.

2. The method of claim 1, wherein:
the organic solvent is selected from the group consisting of isopropanol and ethanol.

3. The method of claim 1, wherein:
the bead substrate is hydrophilic.

4. The method of claim 1, further comprising:
a plurality of the bead substrates each comprising a population of nucleic acids obtained by a previously executed process of nucleic acid amplification from a single nucleic acid molecule within one of the aqueous droplets, wherein the population of nucleic acids is attached during the process of amplification onto the surface of the bead.

5. The method of claim 1, wherein:
the inorganic salt is selected from the group consisting of NaCl, KCl, LiCl, $Na_2SO_4$, potassium carbonate, and ammonium sulfate.

6. The method of claim 1, wherein:
the inorganic salt is introduced in a granular form.

7. The method of claim 1, wherein:
the inorganic salt is introduced in a solution form.

8. The method of claim 1, further comprising wherein:
the bead substrate immobilized nucleic acids are collected in step d) by filtration of the first phase obtained in step c).

9. The method of claim 1, further comprising:
introducing a liquid material which is capable of forming a third phase between the first phase and the second phase to produce a gap phase.

10. The method of claim 9, wherein:
the liquid material comprises a silicone oil.

* * * * *